(12) United States Patent
Mirza

(10) Patent No.: US 10,638,957 B2
(45) Date of Patent: May 5, 2020

(54) INTERNET-BASED DISEASE MONITORING SYSTEM

(71) Applicant: M. Zubair Mirza, Rochester, NY (US)

(72) Inventor: M. Zubair Mirza, Rochester, NY (US)

( * ) Notice: Subject to any disclaimer, the term of this patent is extended or adjusted under 35 U.S.C. 154(b) by 1200 days.

(21) Appl. No.: 14/854,031

(22) Filed: Sep. 14, 2015

(65) Prior Publication Data
US 2016/0103966 A1    Apr. 14, 2016

Related U.S. Application Data

(63) Continuation-in-part of application No. PCT/US2014/025693, filed on Mar. 13, 2014.
(Continued)

(51) Int. Cl.
*A61B 5/09* (2006.01)
*A61B 5/00* (2006.01)
(Continued)

(52) U.S. Cl.
CPC .............. *A61B 5/09* (2013.01); *A61B 5/0022* (2013.01); *A61B 5/0873* (2013.01);
(Continued)

(58) Field of Classification Search
CPC ........ G06Q 30/04; G16H 40/60; G16H 40/63; G16H 50/20; H04N 21/8547;
(Continued)

(56) References Cited

U.S. PATENT DOCUMENTS 5,704,366 A    1/1998  Tacklind et al.
5,816,246 A *  10/1998  Mirza ................. A61B 5/09
                                              600/539
(Continued)

FOREIGN PATENT DOCUMENTS

GB    2295650 A    6/1996
JP    2003204941 A    7/2003
(Continued)

OTHER PUBLICATIONS

European Search Report dated Jan. 7, 2019 for related European Patent Application No. 1819800739.
(Continued)

*Primary Examiner* — Jacqueline Cheng
*Assistant Examiner* — Tho Q Tran
(74) *Attorney, Agent, or Firm* — Bekiares Eliezer LLP

(57) ABSTRACT

An Internet-based disease monitoring system may include a network-based disease sensor device, which is coupled to a sensor, such as a spirometer. A remote server may be coupled to the network-based disease sensor device to provide analysis of input signals from the sensor. The remote server may be able to provide various services for grouping or handling functions relating to such input signals. A service may provide the ability to aggregate input signals from multiple sensors coupled to sensor devices and provide predictive modeling or statistical analysis, which may then be used to adjust future input signals. A service may also contain instructions how to handle billing based on usage of the network-based disease sensor device.

7 Claims, 11 Drawing Sheets

Related U.S. Application Data

(60) Provisional application No. 61/785,696, filed on Mar. 14, 2013.

(51) Int. Cl.
   *A61B 5/087*     (2006.01)
   *G06F 19/00*     (2018.01)
   *G16H 40/63*     (2018.01)
   *G16H 40/60*     (2018.01)
   *A61B 5/08*      (2006.01)

(52) U.S. Cl.
   CPC ......... *G06F 19/3418* (2013.01); *G16H 40/60* (2018.01); *G16H 40/63* (2018.01); *A61B 5/08* (2013.01); *A61B 5/6898* (2013.01); *A61B 2560/0443* (2013.01); *A61B 2562/0204* (2013.01); *A61B 2562/0247* (2013.01)

(58) Field of Classification Search
   CPC ....... A61B 5/0022; A61B 5/0873; A61B 5/09; A61B 2562/0204; A61B 2560/0443; A61B 2562/0247; A61B 5/6898; G06F 19/3456; G06F 19/3418
   See application file for complete search history.

(56) References Cited

U.S. PATENT DOCUMENTS

| | | | |
|---|---|---|---|
| 5,906,203 A | 5/1999 | Klockseth et al. | |
| 6,730,927 B1* | 5/2004 | Smith ...................... | G01F 1/20 128/204.22 |
| 8,333,709 B2 | 12/2012 | Wang | |
| 8,966,235 B2* | 2/2015 | Dicks ...................... | G06F 8/61 713/2 |
| 2002/0134927 A1* | 9/2002 | Kudo ..................... | G01D 5/347 250/231.13 |
| 2006/0036134 A1* | 2/2006 | Tarassenko ......... | G06F 19/3418 600/300 |
| 2007/0103437 A1* | 5/2007 | Rosenberg .......... | G09B 23/285 345/161 |
| 2008/0246629 A1 | 10/2008 | Tsui et al. | |
| 2008/0269673 A1 | 10/2008 | Butoi et al. | |
| 2009/0054737 A1 | 2/2009 | Magar et al. | |
| 2009/0268914 A1 | 10/2009 | Singh | |
| 2010/0315225 A1 | 12/2010 | Teague | |
| 2011/0022025 A1 | 1/2011 | Savoie et al. | |
| 2011/0125045 A1* | 5/2011 | Scholz ................... | A61B 5/087 600/538 |
| 2011/0137141 A1 | 6/2011 | Razoumov et al. | |
| 2012/0029376 A1 | 2/2012 | Weng et al. | |
| 2012/0105200 A1 | 5/2012 | Yoo et al. | |
| 2013/0053657 A1 | 2/2013 | Ziarno et al. | |
| 2013/0053719 A1 | 2/2013 | Wekell | |
| 2015/0273165 A1* | 10/2015 | Hadash ............. | A61M 15/0065 128/203.14 |
| 2016/0021930 A1* | 1/2016 | Minskoff .............. | A61M 15/06 131/329 |

FOREIGN PATENT DOCUMENTS

| | | |
|---|---|---|
| JP | 2003245254 A | 9/2003 |
| JP | 2004054489 A | 2/2004 |
| JP | 2004234118 A | 8/2004 |
| JP | 2005511184 A | 4/2005 |
| JP | 2005538794 A | 12/2005 |
| JP | 200911975 A | 5/2009 |
| WO | 2009052828 A2 | 4/2009 |
| WO | 2012038903 A2 | 3/2012 |

OTHER PUBLICATIONS

Office Action received in related Chinese Patent Application No. 201480021270.9 dated Jan. 17, 2018.

International Search Report and Written Opinion dated Nov. 3, 2014 of related International Patent Application No. PCT/US2014/025693.

European Search Report dated Sep. 23, 2016 for related European Patent Application No. 14774248.0.

* cited by examiner

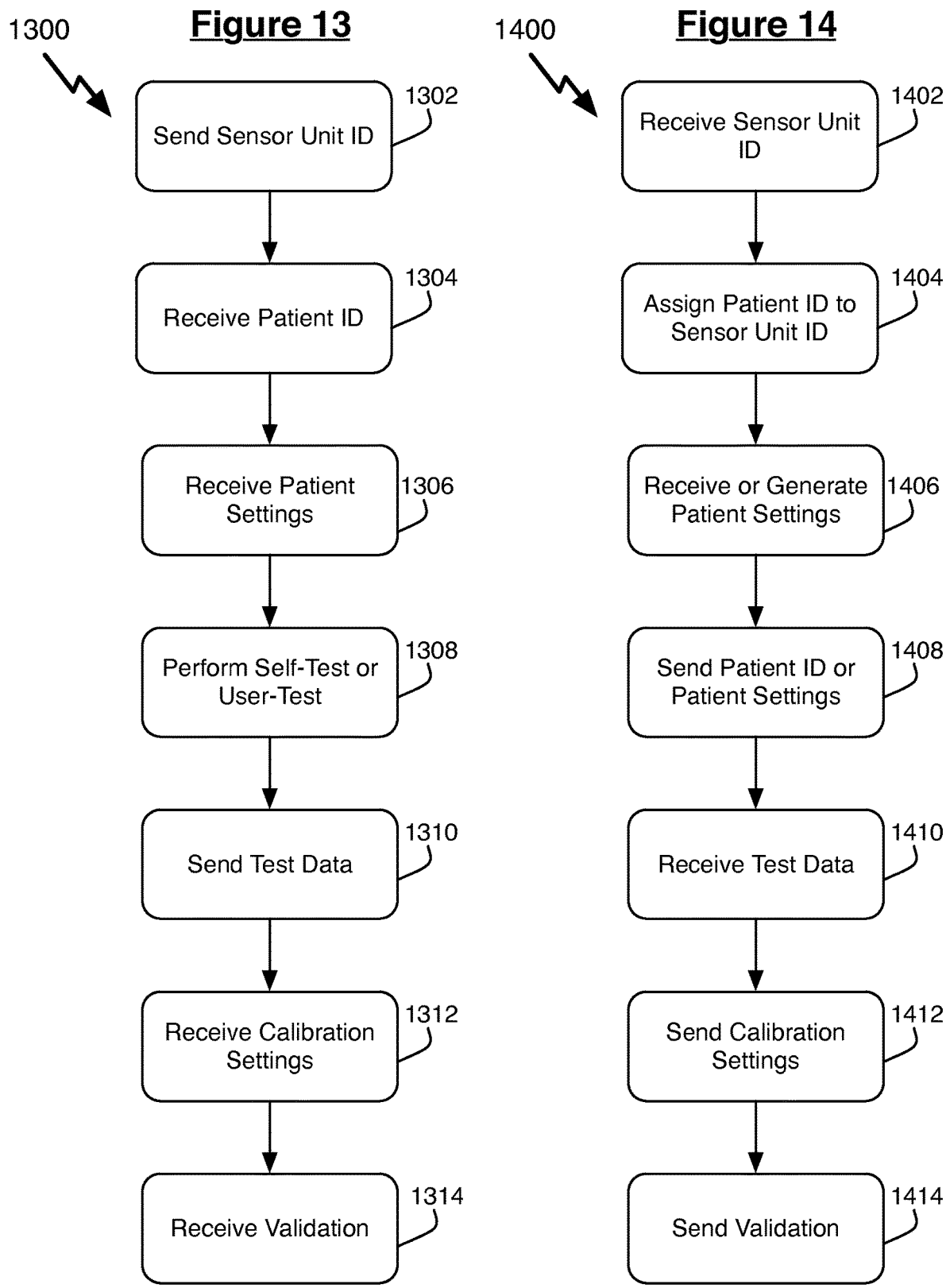

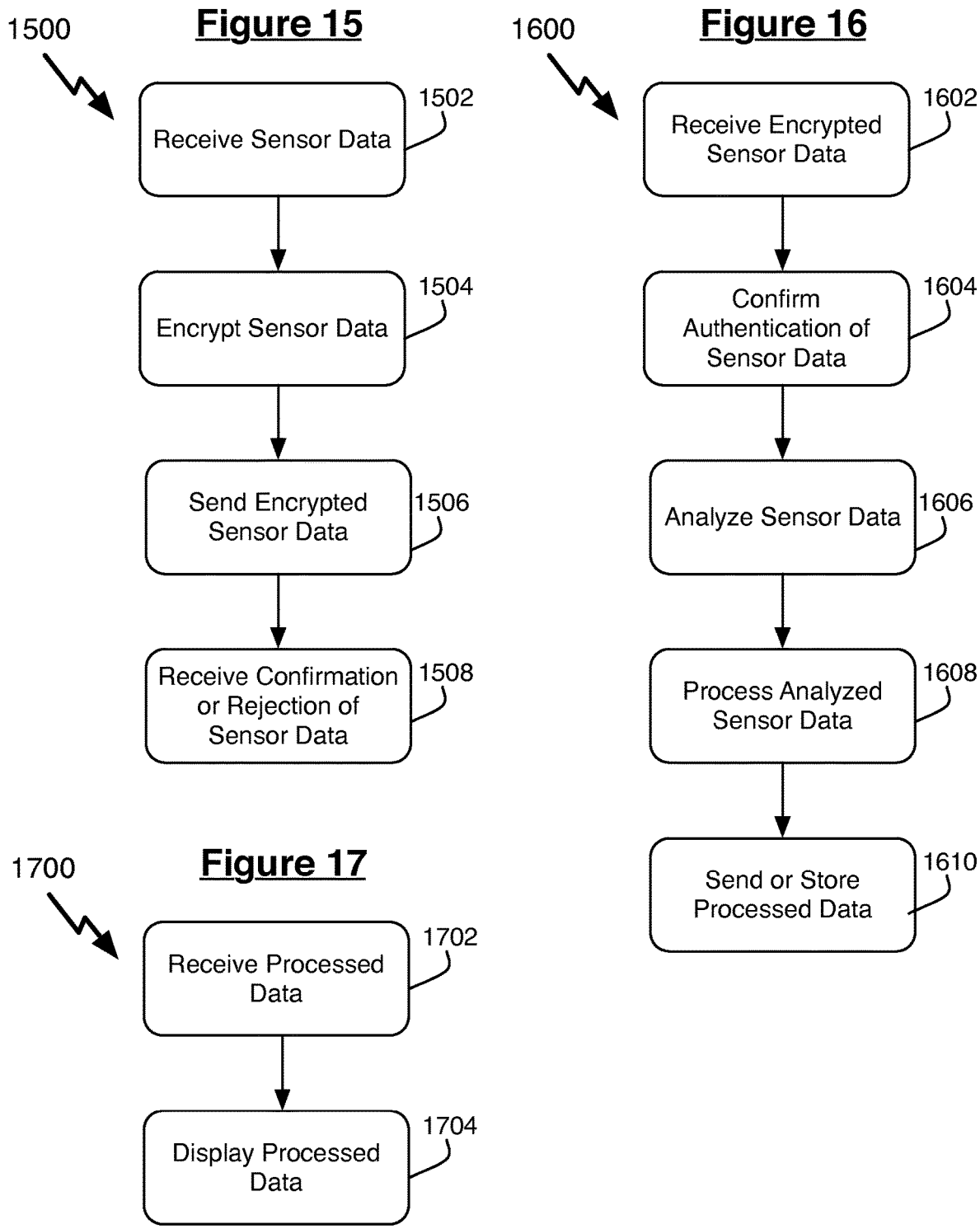

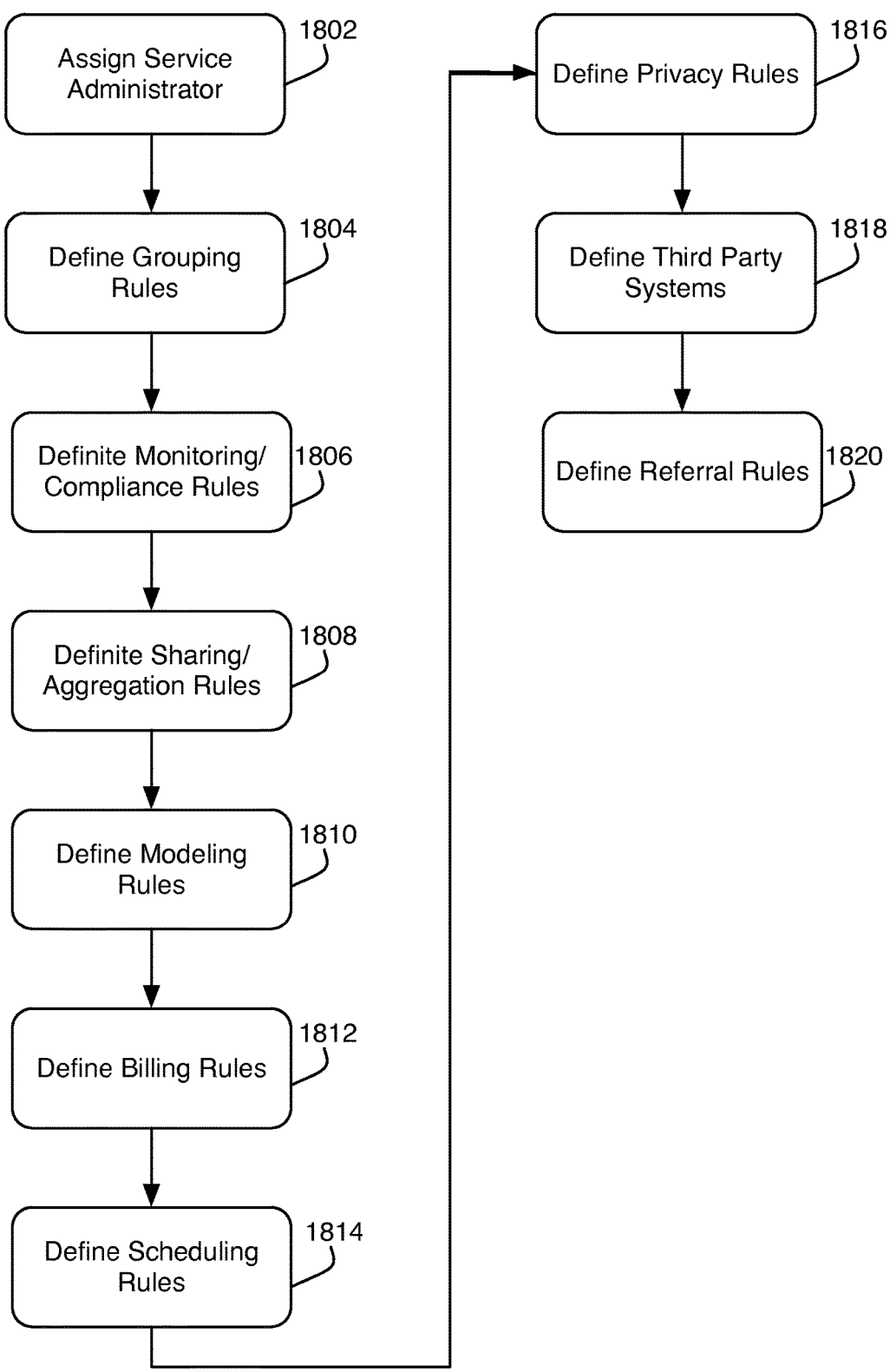

INTERNET-BASED DISEASE MONITORING SYSTEM

CROSS REFERENCE TO RELATED APPLICATIONS

This application is a continuation-in-part of PCT Patent Application No. PCT/US2014/025693, filed Mar. 13, 2014, which claims the benefit of and priority to U.S. Provisional Patent Application No. 61/785,696, filed Mar. 14, 2013, the entireties of which are hereby incorporated herein by reference.

FIELD OF THE INVENTION

The present disclosure relates to effective, efficient, and economical monitoring of diseases in real-time by integrating patient sensors, cell-phone technology, and the Internet in telemedicine and healthcare infrastructure. In particular, the present disclosure relates to a unique configuration of technology for automated patient-run, real-time monitoring of diseases like asthma and chronic obstructive pulmonary disease ("COPD"), as in spirometry, with interactive and real-time communication among the patient, healthcare providers, medical insurance companies, and others via the Internet and mobile communication devices such as personal computers, tablets, and smartphones. The modular configuration of the system allows replacing one sensor module with another to monitor parameters for other ailments such as blood pressure, blood glucose, cholesterol, oxygen saturation, nitric oxide, electrocardiogram ("EKG"), and others.

BACKGROUND OF THE INVENTION

Improving the level of healthcare requires accurate diagnosis and more frequent monitoring of health conditions. The rising cost of healthcare makes it difficult for patients to achieve such higher levels of healthcare. As patients become more educated about their health, more of the high tech miniaturized electronic technologies become affordably available.

Achieving higher efficiency, greater frequency of monitoring, higher performance, real-time communication, minimized maintenance, and lower costs as well as the reduced burden of carrying various portable devices will greatly enhance healthcare quality. Patients with multiple diseases to be monitored require multiple instruments to be carried, in addition to other consumer devices like cellular phones. A lot of functionality is redundant in the various instruments and devices. One aspect of the present invention aims to efficiently consolidate and utilize the commonalities of function and redistribute it to achieve optimum cost, ease of use, and greater functionality most comprehensively. By way of example, this aspect of the present invention provides an Internet-based disease monitoring system ("IDMS") that can be utilized for most critical and commonly monitored ailments and conditions. The redistribution is aimed at allocating technical complexities and costs such that all component, process, and system nodes are well integrated for optimum results with the patient end being the most compact and least costly for maximum ease and utility.

Recently there have been advancements in the field of telemedicine such as eHealth, electronic medical record/electronic health record ("EMR/EHR"), Healthcare informatics and personal connected healthcare, enabling the use of mobile communication devices (such as smartphones) to connect existing medical devices (such as glucometers and pulse oxymeters) to Internet-based servers for uploading data to patient records. However, since all the computations are currently conducted on full-function devices, any upgrades to the system require changing the device or physically upgrading it. There is limited ability to integrate the various nodes in the healthcare spectrum. The user is still required to carry each device along with the smartphone, with the inherent redundancy of the device housing, microprocessor, software, display, keypad, electronics, etc.

SUMMARY

According to one aspect of the present invention, an Internet-based disease monitoring system includes a patient-operated device that includes a sensor module and a transmitter module. The sensor produces input signals responsive to a patient condition, and the transmitter is coupled to the sensor and produces output signals corresponding to the input signals produced by the sensor. A mobile communication device (such as a cell phone) is responsive to wireless receipt of the output signals from the patient-operated device and forwards the output signals to a predetermined network address. A remote server at the network address is responsive to the output signals received from the mobile communication device and analyzes the output signals. The remote server further produces analysis signals representing the results of the analysis, and transmits the analysis signals to predetermined recipients associated with the patient-operated device.

According to another aspect of the invention, an Internet-based method for monitoring disease includes producing, via a sensor of a patient-operated device, input signals responsive to a patient condition. Output signals corresponding to the input signals are transmitted via a transmitter of the patient-operated device. The output signals are further forwarded, via a mobile communication device, to a predetermined network address. The output signals are analyzed, via a remote server at the network address, and analysis signals representing the results of the analysis are produced. The analysis signals are transmitted, via the remote server, to predetermined recipients associated with the patient-operated device.

According to yet another aspect of the invention, a device is directed to determining body function parameters based upon the movement of a patient's breath. The device includes two modules, i.e., a sensor module and a transmission module. The sensor module includes a sensing element and a biasing element. The transmission module includes a light source, a light receiver, a transducer, a processor, and a wireless transmission component (such as Bluetooth or ZigBee). The housing forms a flow chamber having a first port in which a human breath is accepted and a second port from which the breath is exhausted. The flow chamber further has an interior surface. The sensing element is movably mounted within the flow chamber and moves bi-directionally in response to pressure from the exhaled breath received from the patient into the first port and in response to pressure due to the breath inhaled by the patient through the flow chamber. The biasing element resists movement of the sensing element and returns the sensing element to a home position in the absence of any pressure from the exhaled or inhaled breath. The light source transmits a light beam onto the interior surface of the flow chamber. The light receiver receives light reflected off the interior surface. The receiver is stationary while the source of the light directed onto the interior surface of the flow chamber is mounted for movement with the sensing element as the sensing element is moved within the flow chamber. The transducer is coupled to the light receiver and converts the reflected light into electrical signals. The processors receive and process the electrical signals, and determine, in response to the pressure from the breath, the extent of the movement of the sensing element. In response to determining the extent, velocity, and direction of the movement, the processor further determines the magnitude of the pressure.

According to yet another aspect of the invention, a device is directed to determining body function parameters based upon the movement caused by a human breath. The device includes a base, a housing, a sensing element, a biasing element, at least one microphone, an acoustic emitter, an acoustic receiver, a transducer, and a processor. The housing is detachably mounted to the base and forms a flow chamber having a first port in which a human breath is received and a second port from which the breath is exhausted during the exhalation maneuver. The sensing element is movably mounted within the flow chamber and moves in response to pressure from the breath received in or out through the flow chamber. The biasing element resists movement of the sensing element and returns the sensing element to a home position in the absence of any pressure from breath received into the first port. The microphone detects acoustic signals generated by the human breath and the acoustic emitter emits acoustic signals onto the sensing element within the flow chamber. The acoustic receiver receives the acoustic signals reflected off the sensing element as the sensing element is displaced by the pressure of the breath. The transducer is coupled to the acoustic receiver and converts the acoustic signals into electrical signals based on the extent, velocity (rate of displacement/movement), and direction of the air flow. From this raw data, the server computes the volume, rate of breath flow, and other calculated respiratory function parameters.

BRIEF DESCRIPTION OF THE DRAWINGS

Additional aspects of the invention will be apparent to those of ordinary skill in the art in view of the detailed description of various embodiments, which is made with reference to the drawings, a brief description of which is provided below.

FIG. 13 is an example of a methodology for configuring a Sensor Unit.

FIG. 14 is another example of a methodology 1400 for configuring a Sensor Unit.

FIG. 15 is an example of a methodology for sending sensor data.

FIG. 16 is an example of a methodology for receiving sensor data.

FIG. 17 is an example of a methodology for receiving and displaying processed data.

FIG. 18 is an example of a methodology for defining a service.

Figure 1:
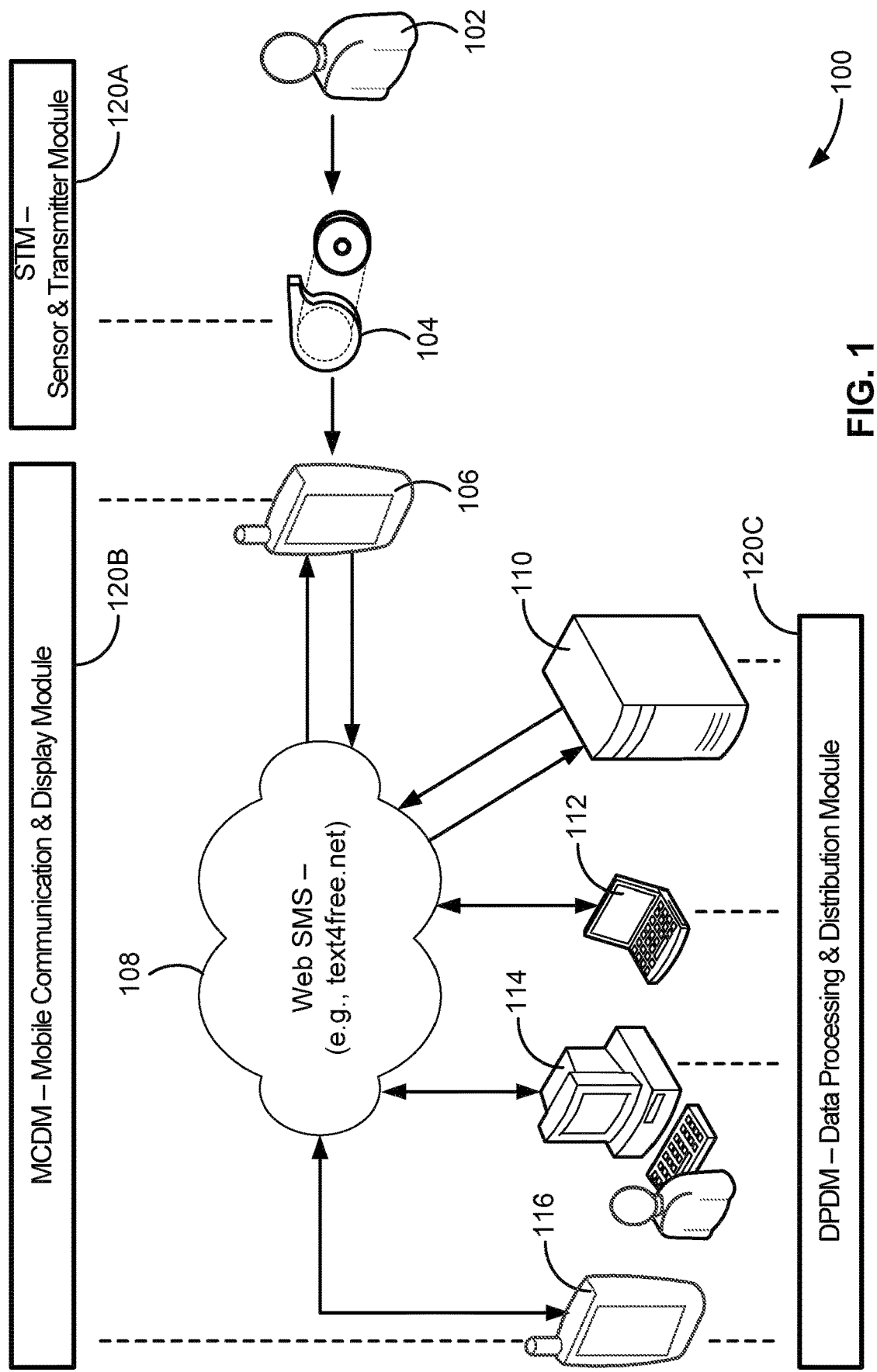
FIG. 1 is a diagrammatic illustration of one embodiment of a telemedicine system with various software modules embodying the invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is intended to cover all modifications, equivalents, and alternatives falling within the spirit and scope of the invention as defined by the appended claims.

DETAILED DESCRIPTION OF ILLUSTRATED EMBODIMENTS

Although the invention will be described in connection with certain preferred embodiments, it will be understood that the invention is not limited to those particular embodiments. On the contrary, the invention is intended to cover all alternatives, modifications, and equivalent arrangements as may be included within the spirit and scope of the invention as defined by the appended claims.

Most medical diagnostic or monitoring instruments typically include (1) a front-end sensing module (with a specific sensor and related signal processing circuitry), (2) an electronic system module (composed of a keypad, display, microprocessor, etc.). (3) a software module (for analysis of measurements and other parameters, etc.) and (4) a communication module to connect all the modules to each other and to convey the data or the results of the analysis—often manually—to the physician, the insurance company, etc.

One aspect of the present invention is directed to reducing a medical instrument, related to personal healthcare monitoring, to its major modules. The front/patient-end module includes a sensor system (for the specific monitoring parameter) that is simple, inexpensive, affordable, and easy to use and carry. The raw data, whether digital or analog, is amplified, conditioned, and converted to a standard signal, which includes a specific device identifier. This data is communicated wirelessly or via a wired connection to a mobile communication device such as a smartphone, a PC, a tablet, a PDA, etc. via an application downloaded to the mobile communication device. The data is generally in the same form as a typical voice/acoustic or text data signal that is communicated to a mobile communication device, so that the signal is universally applicable to all mobile communication devices (which are primarily designed to transmit and receive voice/acoustic or text data).

The application directs the incoming signal to a specific website or network address that recognizes the device and automatically analyzes the signal. The results are transmitted from the server to various locations in relevant formats—to the patient, the clinic/hospital, electronic medical record ("EMR") repository, electronic health record ("EHR") repository, the physician, the insurance company, etc. With the "whole" system approach illustrated by features of the present invention, including the Internet-based disease monitoring system described below, the cost, bulk, and complexity of the system is consolidated and redistributed away from the patient-end toward the server and infrastructure end, where it amounts to a small increment and is more readily tolerated and afforded.

Ongoing relative costs are also redistributed in the form of appropriate subscriptions. For example, simple text/internet link subscriptions are available for the patient, and data-access subscriptions are available to the clinic, physician, insurance company, etc. The system also allows a direct video link between the patient and the physician, for example, via cell-phone cameras or tablet or PC webcams for a more intimate, personalized, and clinically useful assessment of the patient's condition.

FIG. 1 illustrates a system 100 in which a patient 102 uses a spirometer 104 to monitor the patient's respiratory condition. The patient breathes into the spirometer 104, both inhaling and exhaling, and the spirometer automatically detects the displacement and rate (volume and velocity) of air movement through a flow chamber in response to the patient's breathing. The spirometer 104 also produces electrical output signals representing the detected parameters (e.g., volume and velocity), and broadcasts those output signals into a near-field region surrounding the spirometer. In the illustrative system 100, those near-field signals are detected and received by the patient's smartphone 106, which includes an application ("APP") for detecting such signals and transmitting them to predetermined destinations via a network 108 such as the Internet.

In FIG. 1, the potential destinations illustrated are a remote server 110, a health insurance company computer 112, a clinic 114, and/or a physician smartphone 116. The specific destinations to which results and reports are forwarded are selected by the caregiver (physician, clinic/hospital) and saved in the central cloud-based server 110 where computations are conducted, such as automatic processing and authenticated closed-loop for credibility where it may not be subject to patient's accidental or willful changes. Alternatively, the patient's smartphone 106 may be used to preselect, via settings made in the patient's smartphone 106, the specific destinations to which signals received from the spirometer 104 are to be forwarded. The settings are selected via a display generated by the APP in a settings window of the patient's smartphone 106.

The illustrative system 100 includes three software modules: a front-end sensor-transmitter module ("STM") 120A, a mobile communication and display module ("MCDM") 120B, and an Internet-based server for data processing and distribution module ("DPDM") 120C. The STM 120A includes a precise sensor to generate raw signal data and circuitry and/or software for signal conditioning. The raw signal data is optionally encrypted (e.g., using SSL) and transmitted wirelessly (e.g., using Bluetooth or ZigBee at 2.4 GHz). The STM 120A transmits a device ID with encrypted patient-specific header/demographics and raw sensor data in digital/text form to the patient's smartphone 106.

One example of the STM 120A is a pocket electronic spirometer ("PES") for measuring and monitoring pulmonary function, as described in U.S. Pat. No. 5,816,246. As described in more detail below, the sensor may be a simple, low cost, but highly precise (1000-1500 dpi or even greater resolution) device, such as a light-emitting diode ("LED") device or laser-based device. In another example, the sensor is the same as that used in a Bluetooth mouse.

The MCDM 120B includes two specific mobile/cellphone APPs—one for the patient's smartphone 106 and another for the physician's smartphone 116. The APPs are custom written in mobile java or other format for the smartphone 116 to connect to the remote server 110 and to transmit the raw data to the remote server 110 for analysis, distribution, and/or storage.

The DPDM 120C includes the remote server 110, server software modules, sensor-specific computational modules, reporting modules, database archiving (basic web-page, spirometry data, or full interactive web-sys for multiple sensor systems) and PC software module for insurance companies 112, clinics and medical facilities 114, pharmacies 116, etc.

A physician normally prescribes the STM 120A to the patient after initial testing at a clinic or hospital and having determined a specific diagnosis and established norms for the patient. The STM 120A is initiated at the physician's office, with basic patient information and is assigned a record number as a basic identifier for the patient and his/her diagnosis/condition, type of test, etc. The physician also sets certain alarms specific to the patient's condition to serve as reminders or warning alerts that immediate physician attention is required.

Desired parameters are calculated and formatted on the remoter server 110 in various formats for the patient, the clinic record, the physician, EMR/EHR database, medical insurance company, etc. The parameters are further optionally formatted in any other desired format previously identified and saved on the remote server 110. The remote server 110 automatically directs data in appropriate formats to appropriate nodes of the system 100. For example, the patient receives the most simplified version appropriate for self-monitoring and management of the disease or condition with any applicable medical advice based on the results. Detailed data is transmitted to the clinic, appropriate formatted data is transmitted to the EMR/EHR database, and financial and reimbursement related data is transmitted to the insurance company in an appropriate billing format. If the patient parameters are in the warning alarm range, appropriate personnel are alerted and alert messages are automatically transmitted to the clinic/hospital 114, the physician's smartphone 116, and the patient's smartphone 106.

Figure 2:
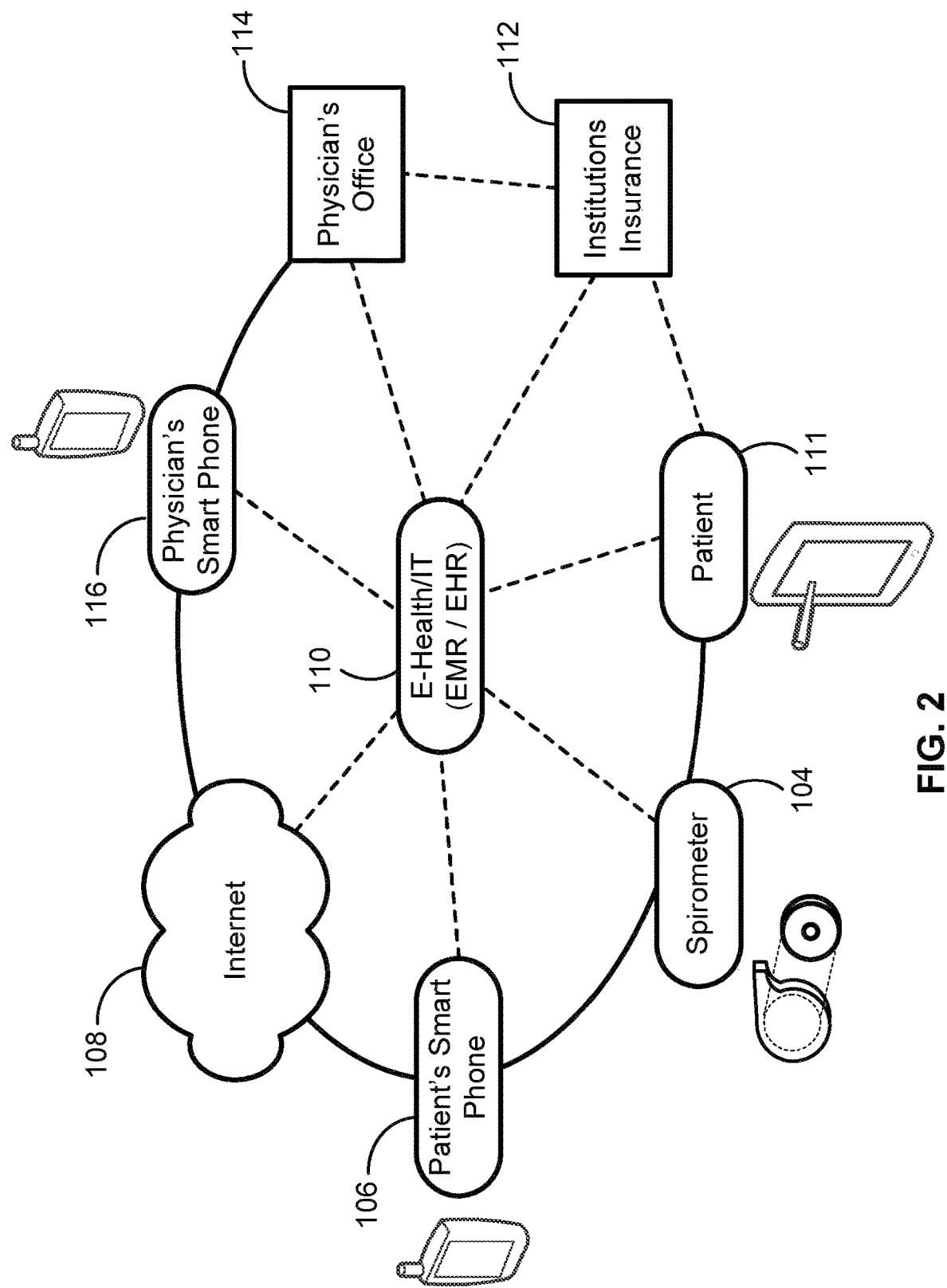
FIG. 2 is a diagrammatic illustration representing the operation of a telemedicine system illustrated in FIG. 1.

Referring to FIG. 2, the system 100 is further interconnected in a hub-and-spoke configuration such that each component and/or device is directly and/or indirectly communicatively coupled with one or more of the other components and/or devices. For example, the patient's smartphone 106 (e.g., a cellular phone) communicates directly with the spirometer 104 and the Internet 108, and is optionally also connected to an eHealth server 110. Similarly, a patient tablet 111 communicates directly with the spirometer 104 and is optionally connected to the eHealth server 110 and/or computers of medical insurance companies 112. The patient tablet 112 may provide the patient additional options and/or a more user-friendly interface than the patient's smartphone 106.

Figure 3:
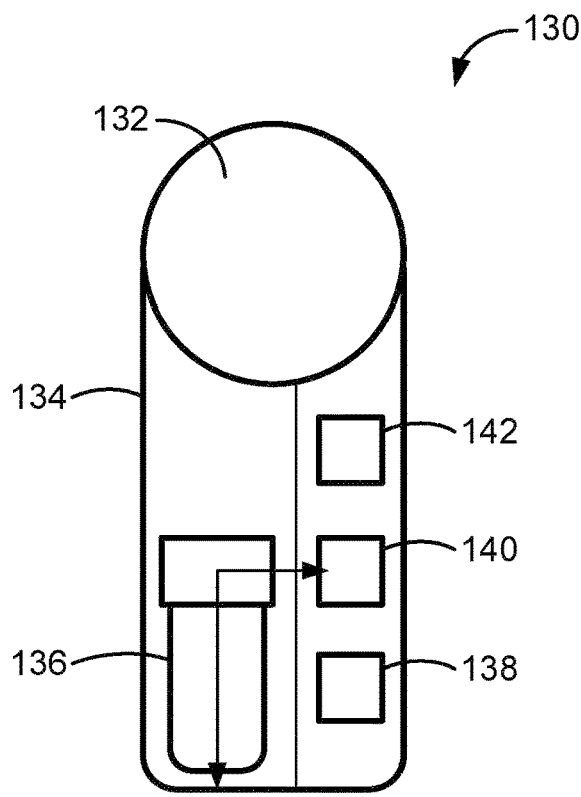
FIG. 3 is a diagrammatical illustration of a sensor and transmitter module ("STM") for use by a patient.
Figure 3A:
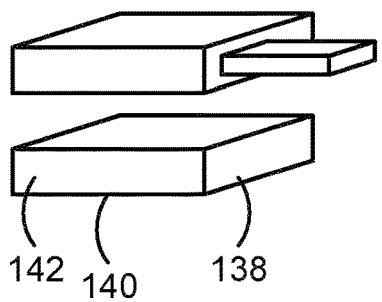
FIG. 3A is a diagrammatical illustration of a sensor and transmitter module ("STM") for use by a patient.
Figure 3B:
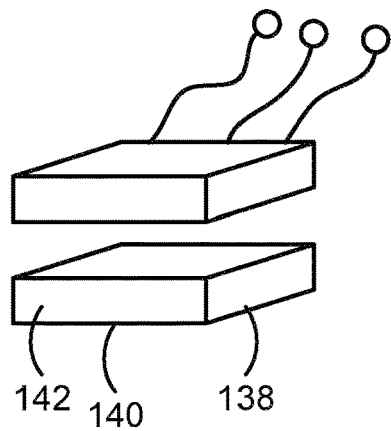
FIG. 3B is a diagrammatical illustration of a sensor and transmitter module ("STM") for use by a patient.
Figure 3C:
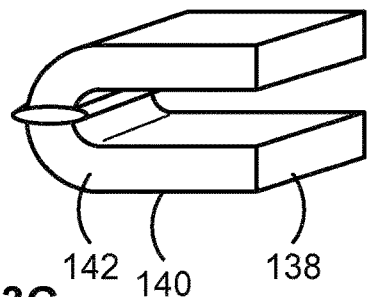
FIG. 3C is a diagrammatical illustration of a sensor and transmitter module ("STM") for use by a patient.

Referring to FIG. 3, an illustrative STM 130 includes several sub-modules and/or components, including a flow-chamber mouthpiece 132, a flow-chamber housing 134, a spring-loaded vane 136, a digital signal processor ("DSP") 138 (which is positioned at a convenient point on a circuit board), an optical or acoustic sensor system 140, and a transmitter system 142. In general, a patient blows air into the flow-chamber mouthpiece 132, forcing air into the flow-chamber housing 134. The forced air causes movement of the spring-loaded vane 136, the movement being sensed and tracked by the sensor system 140. The sensor system 140 produces signals that are optionally conditioned and/or digitized prior to being transmitted by the transmitter system 142. The processor 138 optionally performs required tasks associated, for example, with the conditioning, digitizing, and/or transmission of the signals. The STM may optionally have a secure feature to ensure only the patient-owner may be able to use the device, such as in combination with the patient's own paired smartphone, to automatically transmit test data.

The sensor system 140 includes one or more patient sensors, signal conditioning circuitry, and/or digitization circuitry. The sensor system 140 senses, for example, a patient condition measured by a spirometer, an OEM blood glucose meter, or a cholesterol monitor. The sensor system 140 further senses, by way of a further example, a patient condition associated with blood oxygen saturation ("SpO$_2$"), nitric oxide levels, and other conditions. The flow chamber module may be replaced by specific modules for other disease conditions to connect with the transmitter module to complete the STM patient device.

The transmitter system 142 includes circuitry and/or components, for example, for signal amplification and/or encryption. The transmitter system 142 further includes circuitry and/or components for Bluetooth, Wi-Fi, and/or ZigBee transmissions. As such, the transmitter system 142 can transmit a full range of digital and/or analog data received from a variety of sensors.

Figure 4:
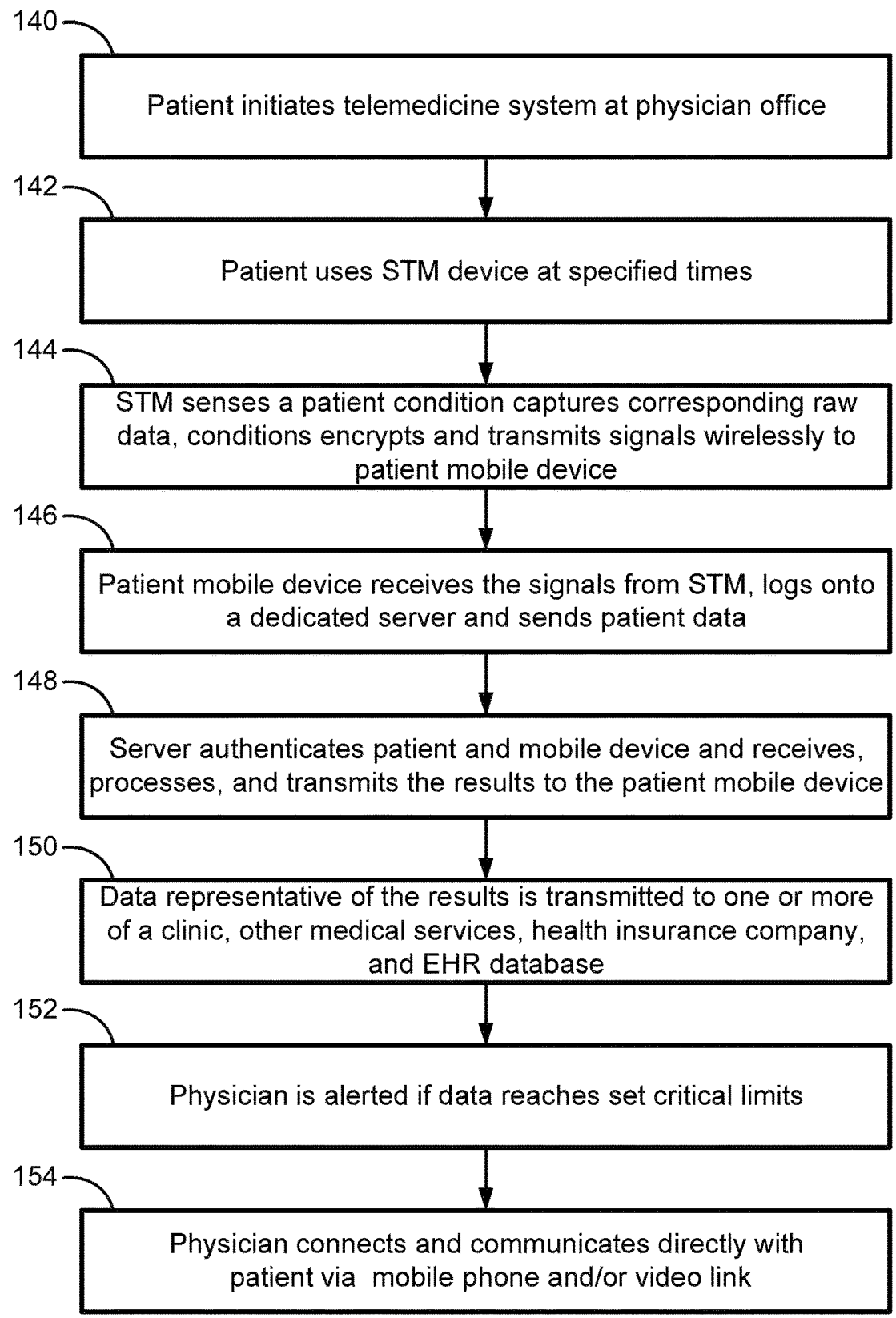
FIG. 4 is a flow chart illustrating the operation of the telemedicine system illustrated in FIG. 1.

Referring to FIG. 4, a method of monitoring a patient condition includes step 140 in which a patient uses the STM at a physician's office to initiate a telemedicine system. Prior to initiating the telemedicine system, the physician tests the patient's respiratory functions to establish and record the patient's baseline spirometry values. To do so, the physician may use a clinic-based IDMS-spirometry module with a disposable breath flow chamber or the patient's own IDMS-spirometry module and flow chamber.

Then the STM, which has a unique serial number embedded for identification, is initialized at the physician's office. For example, the initiating includes setting a patient ID, setting one or more alarms, and setting the specific destinations where the results and/or reports are to be automatically transmitted. The STM is connected with a master clinic-based system associated with the physician and key patient demographics and health information is inputted from the clinic-based system. The information is inputted, for example, by bar code scanning or via a user interface. After relevant data is downloaded, the data is encrypted and embedded in the patient's STM. The physician updates the information as and when needed. Basic patient demograph-ics and health information embedded in the STM typically includes one or more of the following information: (a) a patient identification number; (b) a name, address, and telephone number for the patient; (c) patient gender and age; ((l) patient diagnosis; (e) physician name and identification number; (f) patient's insurance carrier and number; (g) patient's preferred pharmacy and contact information for prescriptions; and/or (h) smoking habits.

At step 142 the patient uses the STM at specified times, e.g., when needed (depending on the patient's condition) or when prompted. For example, the physician instructs the patient to use the STM every morning to monitor the patient's health condition.

At step 144, the sensor system of the STM produces a signal indicative of a patient condition and, in response, the sensor system and/or the transmitter system of the STM condition, encrypt, convert to voice and/or data, and transmit the signal wirelessly or by wire. At step 146, a patient's mobile device (e.g., a smartphone or cellular phone) receives the signal and logs onto a dedicated website server. The server authenticates, at step 148, the patient and/or the mobile device, and receives, processes, and transmits results of the patient condition to the physician and patient mobile devices, and to all other identified destinations.

At step 150 the results are transmitted in the form of data to a clinic where the patient is registered, to other medical services for interpretation, to the patient's medical insurance company, and/or to an EHR medical records database. At step 152 the physician is alerted, for example, by a smartphone and/or a PC if test data reaches set critical limits. The physician connects with the patient via phone and/or video link at step 154 to discuss the results of the monitored condition and advice.

Figure 5:
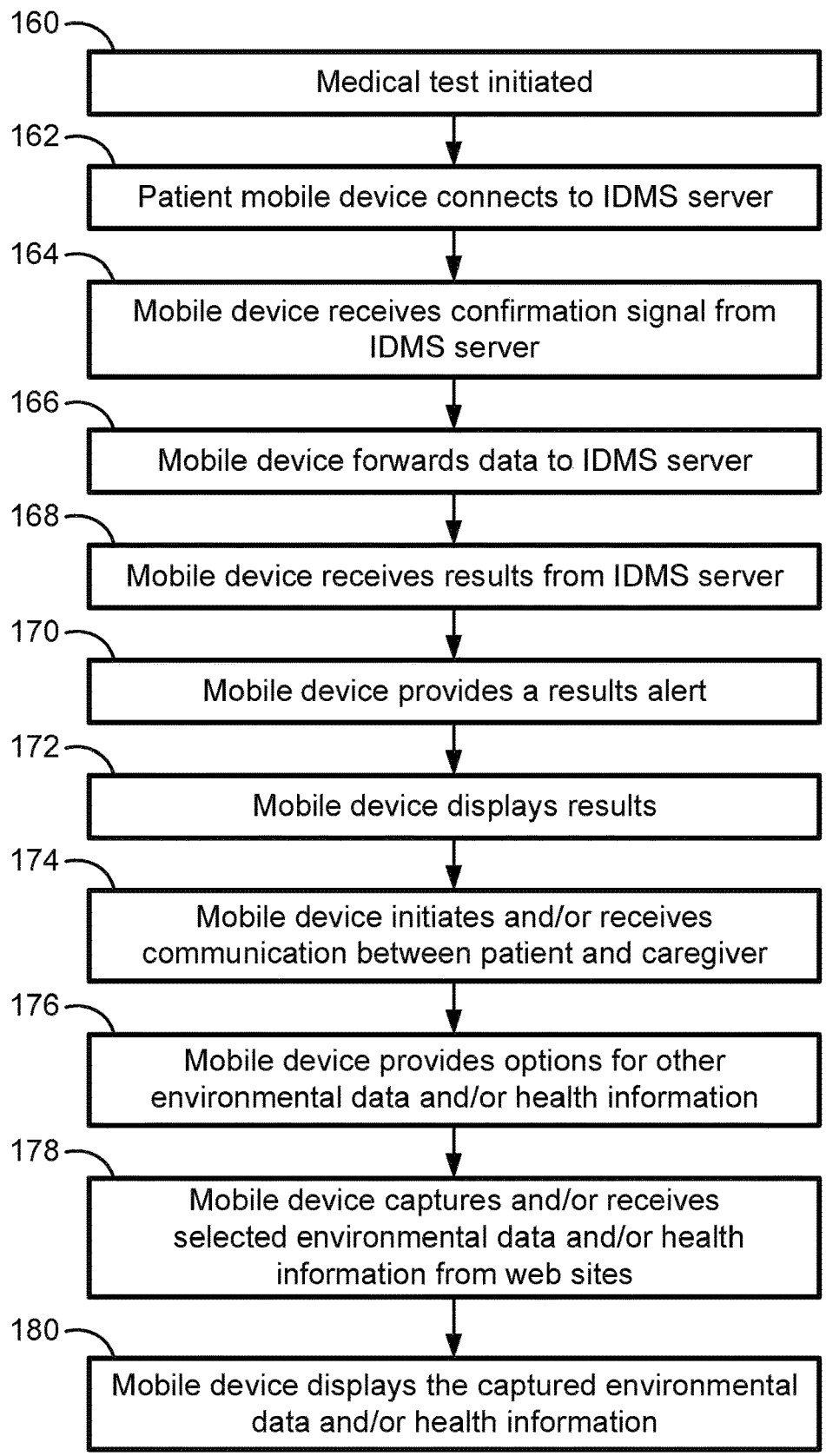
FIG. 5 is a flow chart of an application for enabling a mobile communication device to communicate with an STM.

Referring to FIG. 5, a mobile APP is directed to monitoring a patient condition and includes, at step 160, initiating a medical test. The mobile device (e.g., cellular phone) is awakened in response to receiving an incoming wireless signal (e.g., received via Bluetooth or ZigBee) from the STM upon the patient conducting the medical test. Data representative of the medical test is received by the mobile device.

At step 162 the patient mobile device connects to an IDMS web-based server via an incoming data port. At step 164 the mobile device receives a confirmation signal from the IDMS server. At step 166 the mobile device forwards the data to the IDMS server. The data is optionally forwarded as encrypted raw data.

At step 168 the mobile device is awakened by a signal from the IDMS server that incoming results are being or have been sent by the IDMS server. For example, the mobile device receives a confirmation text message from the IDMS server that the results are completed.

At step 170 the mobile device alerts the patient that the results have been received. For example, the mobile device generates an audio and/or visual alert in the form of a text message to alert the patient.

At step 172 the mobile device displays the results in a default test data format or in a format specified by a physician. The displaying can be, for example, as simple as opening a text message to view the results.

At step 174 the mobile device facilitates a communication connection between the patient and the caregiver (e.g., the patient's physician, clinic, or hospital). For example, upon selection of an icon on a screen of a smartphone or a button on a cell phone keypad, the patient connects with the caregiver and talks or leaves a voicemail or text message. If a voicemail or text message is left with the caregiver, an incoming call or message from the caregiver is subsequently signaled on the mobile device, allowing the patient to receive and respond after authenticating by the patient. Patient log-in information may be enabled or disabled, depending on selected security preferences. Optionally, a unidirectional or bi-directional video communication is initiated with the caregiver. The video communication may include turning on respective cameras on mobile devices for the patient and/or the caregiver.

At step 176 the mobile device provides options for patient selection of other environmental data and/or health information. For example, the mobile device allows selection of icons for pertinent environmental data and/or other important health information and/or health tips. For example, based on the location of the mobile device (e.g., using GPS coordinates), the options may include information related to ozone level, pollution index, smog level, and heat index acquired from public web sites and/or the server 110.

At steps 178 and 180 the mobile device captures/receives and displays the selected environmental data and/or health information. The displaying of the data/information is presented upon demand and/or with test results.

By way of background, spirometry is measurement of a patient's respiratory condition and capacities. As such, a typical spirometer is an instrument used to measure the inspiratory and expiratory performance of the patient's lungs. Most prior spirometers utilize pressure transducer-based sensors called pneumotachometers to measure pressure variations in a tube of a fixed volume as the breath flows through the tube and to calculate several flow- and volume-based respiratory parameters from the measured pressure variations. Another common previous technique utilizes a turbine inside a breath flow tube. The flow of breath turns the turbine, and the rotation of the turbine's fins is measured by corresponding interruption of an optical beam. These prior techniques require the breath to flow directly over the measurement mechanism, further requiring the use of disposable filters and disposable pressure transducers and/or interfaces to prevent bacterial contamination and clogging of the system due to warm and moist breath of the same or multiple patients. These additional elements affect accuracy of the measurements, requiring constant corrections in the software, and add additional complexity, bulk, and costs to prior spirometer systems. Thus, these systems also require frequent calibrations.

Improved spirometers described below eliminate all the moving parts on the measurement side, other than the vane, making the system simpler, more rugged, and more economical to produce and to own. These improvements allow complete elimination of all moving parts (gears, encoder, etc.) from a main housing. For improved optical configurations described below, the only remaining moving part is the vane inside the flow chamber. For an improved acoustic configuration described below, even the vane is eliminated, leaving no moving parts in the entire system.

Utilizing precision high tech, but extremely low cost, optical sensing components, as used in an optical/laser mouse for cursor control on a computer, the system further improves accuracy through higher resolution. The system functions in much the same way as an optical laser mouse operates, thus improving resolution, accuracy, response time, and reliability, and producing digital signal. This further simplifies the system by eliminating the need for analog-to-digital conversion circuitry and also reducing the potential errors and cost.

Figure 6:
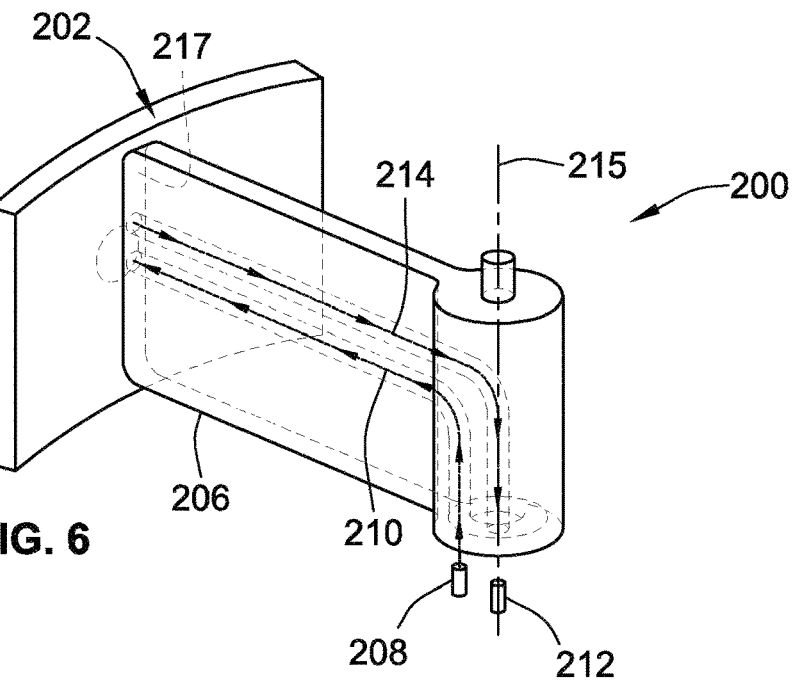
FIG. 6 is a diagrammatic illustration of an STM utilizing a movable vane and an optical sensing system for detecting the velocity and magnitude of the vane movement.

Referring to FIG. 6, and by way of a specific example, an STM is in the form of a spirometer 200 with a flow-chamber 202. The flow-chamber 202 includes an encased spring-loaded vane 206 mounted for pivoting bidirectional movement about an axis 215 in the central portion of the flow chamber, defined by a stationary shaft or stub, in response to the patient's breathing in and out through the flow chamber. According to one example, the flow-chamber 202 is a circular washable and/or disposable plastic flow-chamber housing having inlet and outlet openings to accommodate a patient's breathing through the chamber.

The spirometer 200 includes a light source 208 coupled to a first optical light pipe 210 that extends through the spring-loaded vane 206 so as to emit light from the free end of the vane 206 onto the wall of the flow chamber 202. Light reflected by the wall of the flow chamber is picked up by the end of a second optical light pipe 214 that extends through the vane 206, parallel to the first light pipe 210, to an image sensor 212 such as a charge-coupled device ("CCD") image sensor or a complementary metal-oxide-semiconductor ("CMOS") image sensor. The image sensor 212 tracks bi-directional displacement, caused by breath expiration and/or inspiration, of the spring-loaded vane 206 inside the flow-chamber 202. The image sensor 208 transmits the image to a DSP (such as DSP 138 illustrated in FIG. 3) for analysis.

An initial cracking-point from a resting position of the spring-loaded vane 206, in either direction, sets a system calibration reference point. According to one example, a spirometer has been constructed utilizing PC and computer mouse components and a custom software application in Visual Basic, and a full breath displacement has been captured with a 10 millisecond sampling rate, with captured data being imported into an Excel spreadsheet in which a flow-volume loop and a volume-time graph were developed.

Changes between one image frame and a next image frame are processed by the image processing part of the DSP 138 and translated into movement on two axes. For example, the ADNS-2610 optical mouse sensor manufactured by Agilent Technologies processes 1512 image frames per second, with each image frame being a rectangular array of 18×18 pixels and each pixel sensing 64 different levels of gray. The DSP 138 detects patterns in the images and recognizes how those patterns have moved since the previous image. Based on the change in patterns, the DSP 138 determines how far the vane 206 has moved and transmits the corresponding coordinates to the microprocessor 232. This occurs hundreds of times each second, making the measurement very smooth and able to detect any aberration in the breathing pattern to track the breath precisely.

Instead of using a LED-based emitter 212, an IR laser diode is beneficial because it uses a laser beam with which the measurement is even more precise, giving better response times and tracking. A single-chip optical mouse sensor like STMicroelectronics VT 5365 is optionally used for wireless and Bluetooth applications. This single-chip economical solution provides an internal microprocessor and minimal external circuitry, low power requirement, long battery life, operation with up to 10,000 frames per second, and tracking at up to 40 inches per second.

Another even more effective optical sensor system is a compact (6.8 mm square, 3.86 mm high) Philips PLN2033 "Twin-Eye" laser sensor based on Laser Doppler technology. It is a high-precision, ultra-fast, low-power, small-sized, single-component, laser-based tracking device for use in input and navigation devices like professional PC mice, gaming and CAD applications, and graphical workstations. The PLN2033 "Twin-Eye" laser sensor offers accurate performance over a wide range of speeds and accelerations on virtually all light scattering surfaces covering the demands for applications such as gaming and office applications. It measures changes in position by detection of the scattered coherent laser light that is reflected by a surface, and mathematically by on-chip logic and software, determining the direction and magnitude of the movement up to 3.8 meters per second for each axis (150 inches per second). It is capable of measuring extremely accurately with a re-programmable resolution ranging from 100 CPI to 6400 CPI. The resolution can be re-programmed with an accuracy of 1 CPI.

Figure 7A:
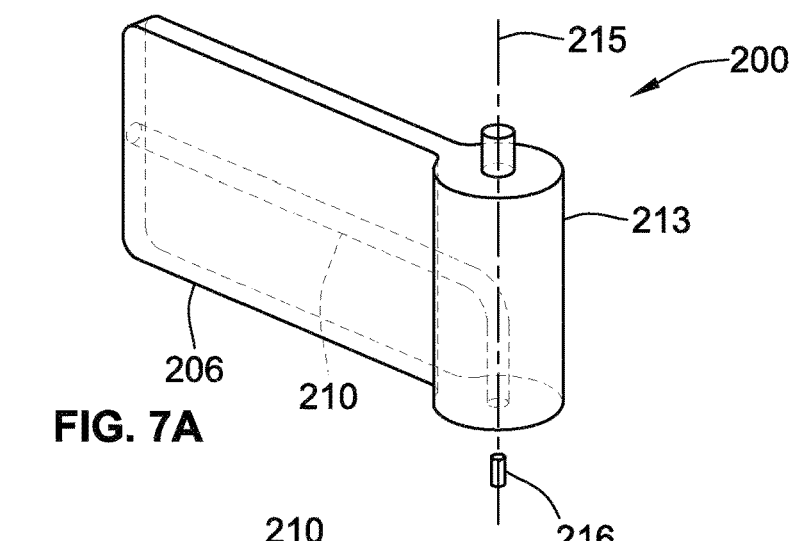
FIG. 7A is a diagrammatic illustration showing a modified STM having an optical light pipe and in which an optical sensor is positioned inside an optical post.
Figure 7B:
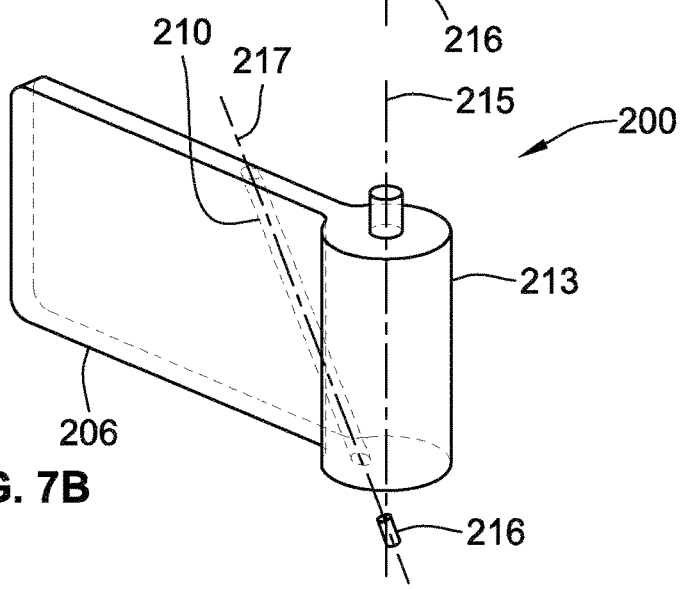
FIG. 7B is a view of the modified STM shown in FIG. 7A with the sensor and transmission modules in a detached state.

Referring to FIGS. 7A and 7B, modified embodiments of the spirometer 200 illustrated in FIG. 6 utilize a combination light emitter/image receiver 216 such as the Philips "Twin-Eye Laser" sensor (PLN2023) or Philips "Laser Doppler" sensor. This combination device 216 permits the use of a single light pipe 210 that both transmits light from the device 216 to the wall of the free end of the vane 206, and picks up light reflected from the wall of the flow chamber 202 and transmits that reflected light back to the device 216. In FIG. 7A, the device 261 and the adjacent end portion of the light pipe 210 are aligned with the axis 215. In FIG. 7B, the device 216 and the light pipe 210 are aligned with an axis 217 that extends diagonally through the vane 206 so as to emit light from the top edge of the vane 206 onto the upper wall of the flow chamber 202. Light reflected back from the upper wall of the flow chamber light is picked up by the light pipe 217 and transmitted back to the device 216. According to one example, the light pipe 217 and the device 216 are oriented at an angle of about 15-30 degrees from a vertical post receiver axis 215.

Figure 8A:
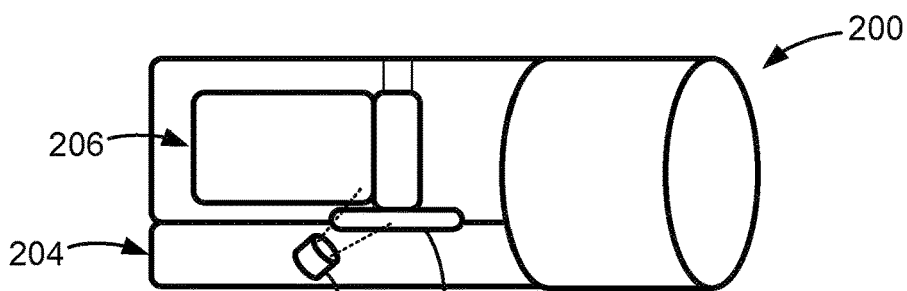
FIG. 8A is a diagrammatic illustration showing another modified STM without an optical light pipe.
Figure 8B:
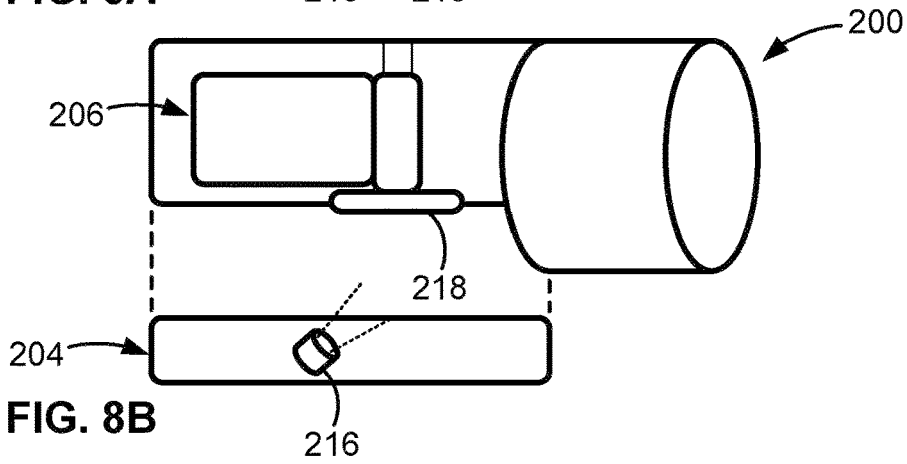
FIG. 8B is a view of the modified STM shown in FIG. 8A with the sensor and transmission modules in a detached state.
Figure 8C:
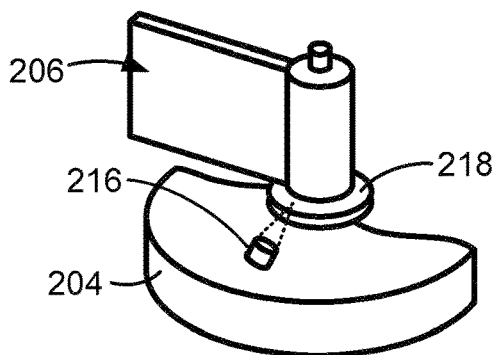
FIG. 8C is a diagrammatic perspective view of the modified STM shown in FIGS. 8A and 8B.

Referring to FIGS. 8A-8C, another modified embodiment of the spirometer 200 illustrated in FIG. 6 utilizes direct pick-up of displacement of the spring-loaded vane 206 without the use of any light pipes. In this embodiment, the combination light emitter/image receiver 216 is mounted on a base 204 adjacent the lower surface of a disc 218 formed as an integral part of the vane 206 so that the disc moves with the vane, thus providing relative movement between the disc and the stationary device 216.

Regardless of the particular optical configuration, thousands of successive pictures of the surface area immediately in front of the image sensor 208 may be captured, with or without a respective optical light pipe conduit. Based on the thousands of images that the image sensor 208 transmits to the DSP 138 for analysis, the DSP 138 detects both patterns and movement of the vane 206. As such, the DSP 138 determines if the vane 206 has moved, and if so, determines the displacement, speed, and direction of the movement. In turn, the speed and movement of the vane 206 in the fixed space within the flow-chamber 202, against the inspiratory and expiratory breath, translate to volume and flow measurements of spirometry.

The acoustic implementations are preferably integrated into the full system in the same way as the optical implementations described above (i.e., using acoustic sensors instead of optical sensors). Thus, they would also include the sensor and the transmission modules and wirelessly communicate the raw data via cellular phone to the cloud/web-based server for analysis and distribution to all the nodes identified earlier. Optionally, both the optical and the acoustic implementations can have a microprocessor in the main housing (as described here) that may send the results to the patient cellular phone and from there still be able to send them to the web-based server to utilize the central monitoring, distribution, and record keeping described earlier.

Figure 9:
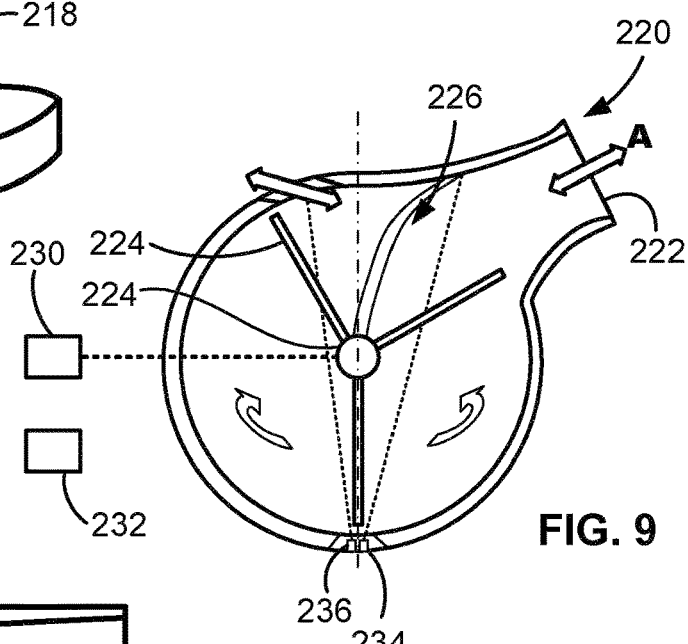
FIG. 9 is a sectional view illustration of an STM utilizing a movable vane and an acoustic sensing system.

Referring to FIG. 9, an acoustic implementation includes a pocket spirometer 220 with a mouthpiece 222 into which a patient blows a breath of air A to drive a vane 224 in a flow chamber 226. The breath of air creates pressure that causes movement of the vane 224, displacing the vane 224 from an initial position. The movement of the vane 224 is sensed by an acoustic sensor system having an acoustic emitter 234 and a microphone 236. The acoustic sensor system utilizes a vane surface to reflect emitted sound (similar to a Doppler effect) as the vane 224 is displaced by the flow of breath air A. The position of the vane 224 is determined and provides a basis for calculating volume and flow rate within the flow chamber 226.

The acoustic sensor system is positioned external to the flow chamber 226 and within a main housing of the spirometer 220 in which other electronic components are mounted. The acoustic sensor system is coupled to the flow chamber 226 via a thin-walled window to maintain a complete bacterial-free separation between the patient's breath and the acoustic sensor system. The flow chamber 226 is optionally detached from the main housing containing electronic components and rinsed for re-use.

The microprocessor 232 provides results to a display of a device, such as an LCD display of a patient mobile device, and stores the results into an associated memory of the device. Upon storing the results to the device memory, the results can optionally be erased from the spirometer memory 230. Optionally, the results are stored on other memory devices, including memory cards and/or personal computers.

At the completion of a test, the microprocessor 232 further determines a highest value reached on an expiratory flow curve and displays that value as a Peak Expiratory Flow Rate ("PEFR"). Based on a plot of a flow-time curve, a Forced Expiratory Volume in one second ("FEV1") can be easily calculated. Other parameters such as Forced Vital Capacity ("FVC"), Mid-Expiratory Flow Rate, ("FEF 25-75"), Forced Inspiratory Flow Rate ("FIVC") at 50% ("FIF 50"), and other parameters are similarly measured from the stored data.

Figure 10:
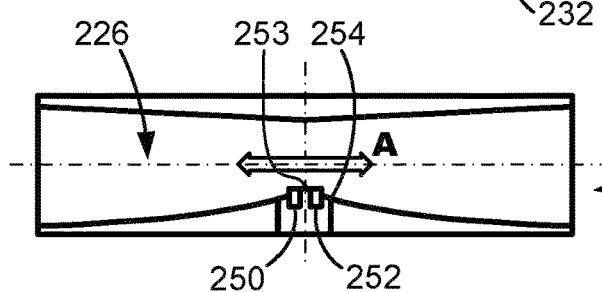
FIG. 10 is a sectional view illustration of a modified STM utilizing an acoustic sensing system without any moving parts.

Referring to FIG. 10, another acoustic implementation eliminates the vane 224 such that the spirometer 220 does not require any moving parts. In this streamlined flow chamber configuration, one or more highly sensitive microphones 250 or 252 are positioned externally across a thin-walled window 253 in the flow chamber 226 to maintain a bacterial-free separation. The inside configuration of the flow chamber includes a ridge 254 in the air flow path that enhances the sound of breath blowing over it.

The microphones 250 or 252 are placed closest to the ridge 254 to maximize the sound quality, which is further enhanced by a conical configuration leading to the ridge. The microphones capture an acoustic signal generated by the patient's breath as it flows against this geometrically optimized internal configuration of the flow chamber.

An acoustic pattern generated by the flowing breath correlates to the flow and volume inside the fixed space of the flow chamber for both expiration and inspiration. The simplified flow chamber is detachable and optionally a disposable or a reusable (e.g., rinse-able) unit. Two microphones, instead of a single microphone, are helpful in determining the direction of flow corresponding to expiration and inspiration.

Figure 11:
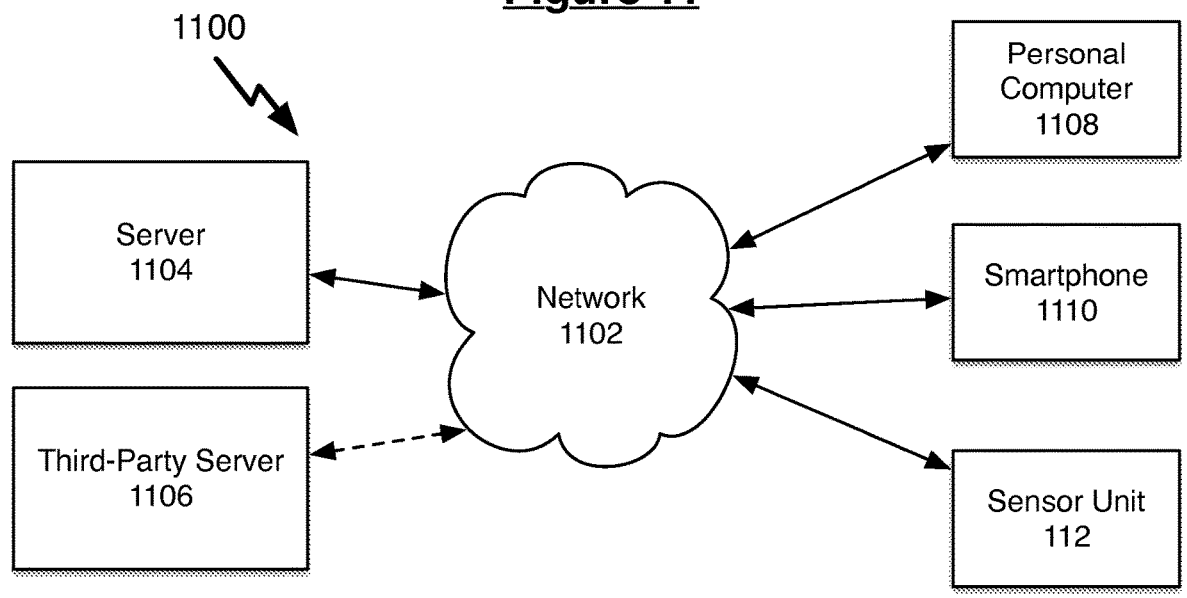
FIG. 11 is another example of a system for an IDMS.

With respect to FIG. 11, another example of a configuration for IDMS is shown. System 1100 may consist of a network 1102, such as the Internet, LTE, etc., which communicatively couples server 1104, third-party server 1106, personal computer 1108, smartphone 1110, and sensor unit 1112. Though only individual examples are shown of the components comprising system 1100, it may contain multiple instances of such components (e.g., several servers, hundreds of sensor units). Sensor unit 1112 may be composed of a simple sensor component communicatively coupled to a network or additionally a smartphone or PC also communicatively coupled to a simple sensor component. Sensor unit 1112 may also be partially or fully integrated with prescription delivery devices (e.g., patient medication use (such as inhaler puffs) can be measured). Server 1104 and sensor unit 1112 may also apply date/time stamps to data recorded or sent/received in order to facilitate services provided by services component 1208 described below.

Figure 12:
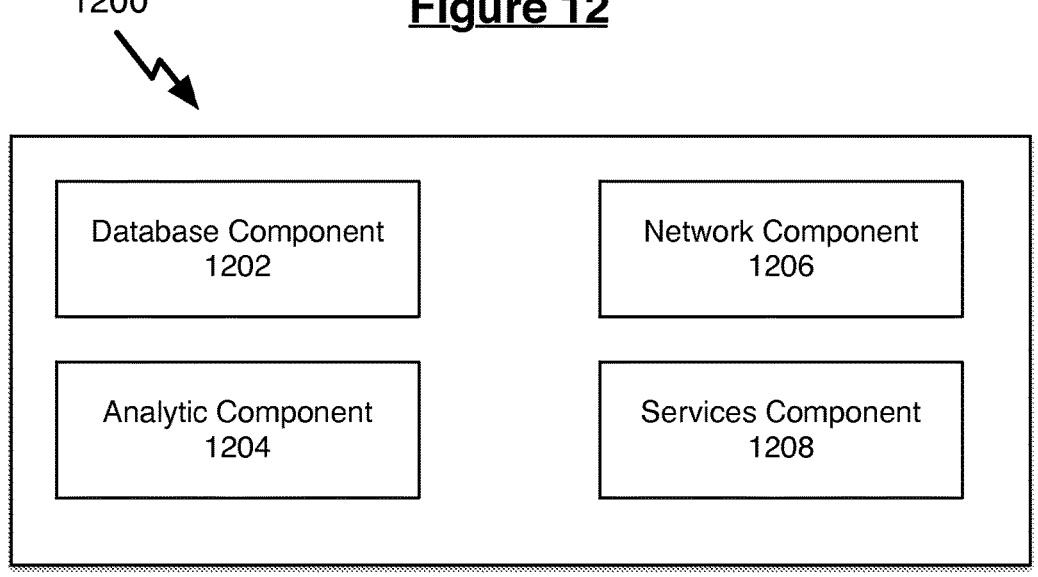
FIG. 12 is an example of the configuration of an IDMS server.

As shown in FIG. 12, an example of the configuration of an IDMS server is shown. System 1200, which may be used for server 1104, may be configured to have a database component 1202, an analytic component 1204, a network component 1206, and a services component 1208. Database component 1202 may be used to store or retrieve data useful to an IDMS, such as raw data received from sensor unit 1112, analytical results from analytic component 1204, messages sent to or from network component 1206, and processed data or other records handled by services component 1208. Analytic component 1204 may be used to handle the analysis of raw data obtained from sensor unit 1112 or may further process analyzed data based on instructions from services component 1208. Network component 1206 may be responsible for handling communications with other systems or devices, such as those shown by system 1100. In addition, network component 1206 may also handle the generation of messages based on information received from database component 1202, analytic component 1204, or services component 1208. Services component 1208 may be used to implement various services provided by the IDMS to patients, doctors, insurance providers, emergency dispatch operators, etc.

With respect to FIG. 13, an example of a methodology 1300 for configuring a sensor unit is shown. At step 1302, the sensor unit may be instructed to send a sensor unit ID, such as via the Internet. The sending of the sensor unit ID may occur when sensor unit 1112 is initialized, reset, or upon being power on. In some embodiments, the sensor unit ID may be assigned to sensor unit 1112 by server 1104 as part of an initialization process (e.g., upon device detection by server 1104). In some embodiments, the sensor unit ID may be programmed permanently into sensor unit 1112, such as a unique identifier stored in firmware. At step 1304, sensor unit 1112 may receive a patient ID, which sensor unit 1112 may use to associate with sensor data obtained from sensor unit 1112. At step 1306, sensor unit 1112 may receive patient settings, which may contain information such as patient data, configuration settings for sensor unit 1112, etc. The patient settings (or patient ID) may also include a cryptographic key or instructions relating to the exchange of a cryptographic key, which sensor unit 1112 may use for encrypting sensor data or other information. At step 1308, the sensor unit 1112 may perform a self-test or a user-operated test of sensor unit 512, which may include generating information useful to calibrating sensor unit 1112. At step 1310, sensor unit 1112 may send the data relating to a self-test or user-operated test. In some embodiments, such data may also be encrypted using information obtained from the patient ID or patient settings. At step 1312, sensor unit 512 may receive calibration settings, such as instructions to modify sensor data or adjusting the operation of sensor unit 512. In some embodiments, steps 1308-1312 may performed more than once, such as where calibration requires sending further test data to determine if a calibration is valid. At step 1314, sensor unit 512 may receive instructions or a notice that it is ready to take measurements.

With respect to FIG. 14, another example of a methodology 1400 for configuring a sensor unit 1112 is shown. At step 1402, a sensor unit ID may be received, such as via the Internet. The sensor unit ID may be unique to a particular sensor unit 1112. At step 1404, sensor unit 1112 may retrieve or generate a patient ID that may be used to associate sensor data with a patient. At step 1406, patient settings, which may contain information such as patient data, configuration settings for sensor unit 1112, etc., may be generated or received. In some embodiments, patient settings may depend on sensor unit ID, patient ID, or information provided by services component 1208. The patient settings (or patient ID) may also include a cryptographic key or instructions for exchanging a cryptographic key, which sensor unit 1112 may use for encrypting sensor data or other information. At step 1408, the patient ID or patient settings may be sent, such as to sensor unit 1112. At step 1410, data relating to a self-test or user-operated test for sensor unit 1112 may be received. In some embodiments, such data may also be encrypted using information obtained from the patient ID or patient settings. At step 1412, calibration settings may be generated or retrieved, such as instructions to modify sensor data or adjusting the operation of sensor unit 512. In some embodiments, steps 1408-1412 may perform more than once, such as where calibration requires receiving further test data to determine if a calibration is valid. Calibration settings generated, retrieved, or sent may also include updates to the software of sensor unit 1112 (e.g., a new smartphone application, new firmware for a simple wireless sensor unit). At step 1414, instructions or a notice may be sent indicating that sensor unit 1112 is ready to take measurements.

With respect to FIG. 15, a methodology 1500 is shown for sending sensor data. At step 1502, sensor data is received, such as from a sensor component on sensor unit 1112. At step 1504, the sensor data may be encrypted, such as via a patient ID or patient settings stored on sensor unit 1112. At step 1506, the encrypted sensor data may be sent, such as from sensor unit 1112 to server 1104 via the Internet. At step 1508, a message may be received confirming acceptance or rejection of the encrypted sensor data. A message indicating rejection data may include a notice that the data was rejected, information describing why the information was rejected, or instructions (such as new settings or an indication to perform calibration) for sensor unit 1112. For example, the message may state that the encryption of the sensor data was incorrect and may also instruct that a new encryption key must be obtained. As another example, the message may provide information indicating that sensor unit 1112 was not operated properly. For example, analysis of the received sensor data on server 1104 may show that the user took an inappropriate action (e.g., too rapid of an exhale) for proper measurement and server 1104 may send an instruction to sensor unit 1112 that the user needs to exhale more slowly into a sensor component). A message indicating confirmation of data may include a notice that the data was accepted, information relating to why the data was accepted, or additional instructions for sensor unit 1112.

With respect to FIG. 16, an example of methodology 1600 for receiving sensor data is shown. At step 1612, encrypted sensor data may be received. For example, server 1104 may receive encrypted data via the Internet. At step 1604, the encrypted sensor data may be authenticated or decrypted, such as by server 1104. As part of the authentication process, the relationship between the encrypted sensor data and a sensor unit ID, a patient ID, or other identifying information may be determined. At step 1606 the decrypted sensor data may undergo analysis, such as by analytic component 1204. For example, the sensor data may only provide metrics over time of airflow, which is then used to form a graph of airflow versus time. The sensor data may also be further analyzed, such as to determine if the sensor data is within certain thresholds. At step 1608, the analyzed sensor data may be further processed, such as from instructions from services component 1208. For example, the sensor data and analysis may be processed to form a patient record that further includes patient information, insurance information, legal or other informational requirements, etc. At step 1610, the processed data may then be sent or stored, such as to a smartphone for display of a graph or to database component 1202 for storage. If the processed data is sent, encryption may be applied to the processed data as described with respect to the sensor data.

With respect to FIG. 17, a methodology 1700 is shown for receiving and displaying processed data. At step 1702, processed data is received, which if encrypted may be decrypted as described with respect to the sensor data. At step 1704, processed data may be displayed, such as on a smartphone that is communicatively coupled with a sensor unit.

In some embodiments, encryption of sensor data or processed data may further include compression of such data. Sensor unit 1112 may be communicatively coupled with a variety of sensor components, such as those that measure or perform pulmonary function testing (e.g., spirometry), EKG, cholesterol, blood glucose, pulse oximetry (blood oxygen saturation ($SpO_2$). Sensor unit 1112 may be able to measure high resolution digitized raw data via a sensor component, then condition such data to comply with patient privacy requirements (e.g., HIPAA) as part of the encryption process. In further embodiments, encrypting sensor data or processed data may include further formatting the data for a particular message medium. For example, if Internet service is not available but instant messaging is available, sensor unit 1112 or network component 1206 may send or receive encrypted messages in the form of encrypted text data sent by instant message. In some embodiments, sensor unit 1112 or network component 1206 may restrict the types of sensor data or processed data that may be sent via a particular message medium. For example, network component 1206 in response to encrypted sensor data sent by instant message may not send encrypted processed data in return, but only may send confirmation as described above.

Services component 1208 may be used to handle a variety of services, which may be arranged by clients, sensor unit types, providers, patients, etc., for handling sensor data from sensor units (e.g., sensor unit 1112) and related activities. These services may be defined according to one or more of the following functions: grouping; monitoring/compliance; sharing/aggregation; modeling; billing; scheduling; privacy; third party systems; and referral.

For example, a service may defined according to grouping functions, wherein the members of the service are defined by one or more sensor IDs, one or more patient IDs, or information related to a patient, provider, insurer, patient's medication, a set of services hosted by services component 1208, etc.

With respect to monitoring/compliance functions, a service may indicate various tasks that must be periodically performed. For example, a service may have access to patient data containing prescription information for a patient. In such embodiments, server 1104 may use such prescription information to send messages to sensor unit 1112, personal computer 1108, or smartphone 1110 containing reminders to take a medication or that a medication has been prepared at a pharmacy and is ready for pickup. In further embodiments, server 1104 may use such prescription information to send messages to sensor unit 1112, personal computer 1108, or smartphone 1110 to trigger a visual or auditory reminder on a prescription appliance (e.g., a flashing LED on a prescription box that is coupled by Bluetooth to sensor unit 1112) or on sensor unit 1112, personal computer 1108, or smartphone 1110. As another example, rules may be set for how often or when sensor data must be received according to sensor unit ID or patient ID associated with a service. For example, if sensor data is not received for a period of time (e.g., 7 days), server 1104 may send messages to sensor unit 1112 to display a message, sound an alarm, etc. that reminds patient to use sensor unit 1112. In addition, server 1104 may also send a message to a patient care provider or other person associated with the patient indicating that sensor data has not been received. In some embodiments, a service may also contain instructions that environmental data be monitored and used to send notifications to sensor unit 1112, personal computer 1108, or smartphone 1110. For example, a service may require that measurements of allergens (e.g., pollen, weeds, etc.), pollution, smog, ozone, heat-index, etc. be monitored based on location-data received from sensor unit 1112 (such as via GPS tracking). Such measurements may be sent periodically to sensor unit 1112, personal computer 1108, or smartphone 1110 by server 1104. In some embodiments, server 1104 may only send such measurements or information relating to such measurements (e.g., instructions to sound an alarm) when such environmental data indicates that an unsafe condition exists for a patient. For example, a provider may have specified that exposure to a certain level of allergens for patients in a service requires the issuance of a message that results in sensor unit 1112 sounding an alarm and displaying a warning to patients to seek a safe environment. In some embodiments, a service may also include instructions related to sending messages regarding preventative measures, such as a periodic notification to sensor unit 1112, personal computer 1108, or smartphone 1110 to record patient's weight, replace disposable components of sensor unit 1112, update a patient diary regarding medication usage or activity, etc.

A service may also be defined according to sharing/aggregation functions, wherein rules may be defined for the sharing and aggregation of sensor data, processed data, or information related to a patient. For example, a service may allow anonymous processed data obtained from sensor data to be shared along with relevant patient medication or treatment history. For example, if a patient is regularly taking a specific form of medication or treatment for diabetes, relevant sensor data or processed data may be shared anonymously to allow aggregation of that data across multiple services. Such aggregation may be handled by another service handled by services component 1208. For example, multiple services operated by different providers may be members of a service that exists to aggregate anonymous patient data they provide and contains instructions for analytic component 1204 on how to process the aggregated data and who may have access to the results. In some embodiments, a service which performs aggregation may be used to provide feedback to other services. For example, the aggregated sensor data may be used to indicate strong deviations in analyzed or processed sensor data of a particular patient belonging to a service that shares data with the aggregation service. In some embodiments, a service may perform its own aggregation functions, such as where patients are divided into two groups where one group uses a placebo and the other a trial medication. In such situations, analyzed or processed sensor data may be aggregated and further analyzed/processed to show trends based on the sensor data, such that meaningful distinctions between the two groups may be observed (e.g., population trends). As another example, aggregate data may allow for the calculation of regional or population statistics, the prevalence of disease within the measured population, outbreaks, etc. As further example, if particular treatments are found to be particular effective against an outbreak based on the aggregate data, such treatments may be shared with according to the rules of a service to help limit the scale of an outbreak.

In some embodiments, services may perform modeling functions based on the aggregation of data. For example, if a patient's analyzed or processed data shows a consistent pattern over a 3 month period, then substantially changes, the service may find similar instances of such substantial changes in aggregated data to predict the consequence of such a change. For example, based on the rate of change in a particular measurement, the service may predict the future rate of change and possibly underlying cause (e.g., creatine levels will increase by 10% per day, likely cause is kidney failure). As another example, aggregate data may also include environmental data related to the location of each sensor unit providing data. In such situations, predictions may be performed based on changes in the environmental data for a particular sensor unit. For example, if the aggregate data shows that increased allergens affects breathing and the environment of a particular sensor unit experiences increased allergens, the service may calculate a prediction of how a patient's breathing may change due to the presence of such allergens. Such environmental predictions based on aggregate data may allow patients or providers to understand the cause of a change in analyzed or received sensor data relating to that patient. In some embodiments, such predictions may also be used to further process analyzed sensor data (e.g., to create a view of analyzed sensor data independent of environmental conditions).

In some embodiments, services may perform billing functions. For example, a service may define the type of billing to be used in association with a patient's use of sensor unit 1112, which may consist of a pay-per-use (e.g., every validated sensor measurement is billed at 5 cents), a subscription service (e.g., $30 per month), pre-paid services, data plans, subsidies, etc. A service may define a variety of different ways that functions or sets thereof performed by the service should be billed. A service may also determine how functions should operate (e.g., suspension, termination, limited access) if adequate credit or funds are not available to cover the costs under such billing rules. A service may also automatically prepare requests for reimbursement for functions performed by the service, which may be submitted electronically (e.g., to an insurer). For example, a service may use patient information (e.g., patient analyzed/processed sensor data, patient condition, diagnosis, physician consultation online, insurance data) to automatically prepare requests for reimbursement for functions provided by the service on the behalf of the patient. As another example, a service that aggregates data from other services and provides predictive modeling to those other services may also have billing rules defined and charges based on those rules automatically prepared and submitted by the aggregation service. In the generation of reimbursement requests, billing rules may also utilize date/time stamps relating to records, such as sensor data, to determine the extent of reimbursement that should be requested.

In some embodiments, services may perform scheduling functions. For example, a service may automate appointment scheduling and reminders with corresponding instructions, which may be then sent to sensor unit 1112, personal computer 1108, or smartphone 1110 and confirmed by a patient using sensor unit 1112, personal computer 1108, or smartphone 1110. In some embodiments, the scheduling rules may also facilitate setting up audio, video, or text connections between sensor unit 1112 and another device. For example, a provider may need to speak to a patient about recent analyzed sensor data and requests for a video conference call. Server 1104 may then send a request to sensor unit 1112, personal computer 1108, or smartphone 1110 that patient accept a video conference call. If patient accepts, then server 1104 may facilitate the setting up of that video conference call.

In some embodiments, services may perform privacy functions. For example, rules may be defined in the service regarding who may access particular data held by the service, what type of data may be shared with other services, the extent to which records must be retained (such as to comply with record retention policies), etc.

In some embodiments, services may perform third party system functions. For example, rules may be defined regarding when and who may access third party systems accessible from a service. In some embodiments, a service may also define rules regarding how information must be translated, formatted, or otherwise be prepared for an exchange with a third party system. For example, if a service has generated a request for reimbursement to a third party system, further rules may define billing codes, encryption, etc. that must be added to the reimbursement so that it is processed correctly by the third party system.

In some embodiments, services may perform referral functions. For example, a service may contain rules for allowing a provider to consult with an expert regarding information held by the service. For example, a general practitioner may observe processed data and wish to contact an expert on the disease being monitored. Accordingly, the service may contain a list of approved experts and conditions the processed data must meet to obtain access to an approved expert. If the service determines that processed data meets such conditions, consultation with an expert may by approved by the service.

With respect to FIG. 18, a methodology 1800 is shown for defining a service. At step 1802, an administrator is defined for the service. For example, an administrator may be a patient, a provider, a support organization for providers, etc. At step 1804, grouping rules for the service may be defined, which specify the members of the service. Members may be defined based on static or dynamic conditions. For example, members of a service may be defined based on patient IDs, sensor unit IDs, patients assigned to a provider, patients using a particular medication, patients assigned to a research study, all sensor unit IDs or patient IDs located in a specific region (e.g., California). In addition, a service may be defined as a member of another service. At step 1806, monitoring/compliance rules of the service may be defined. For example, rules may be set regarding when or how often information required by the service should be received or notices/instructions sent to ensure compliance by members of the service. At step 1808, sharing/aggregation rules may be defined as to how sharing or aggregation of data held by service, such as sensor data received from patients or analysis thereof. At step 1810, modeling rules may be defined as to how data held by the service should be used to predict future conditions or adjust existing data. At Step 1812, billing rules may be defined as to how functions performed by the service should be billed. At step 1814, scheduling rules may be defined, such as determining when appointments should be scheduled or the process for arranging an online consultation. At step 1816, privacy rules may be defined, such as who may access data held by a service and when. At step 1818, third party system rules may be defined. For example, rules stating what third party systems may access from the service, who may access such third party systems, and the conditions for when access to such third party systems may be defined. At step 1820, referral rules may be defined for the service. For example, a set of experts may be defined and conditions set for when an expert may be consulted.

While particular embodiments and applications of the present invention have been illustrated and described, it is to be understood that the invention is not limited to the precise construction and compositions disclosed herein and that various modifications, changes, and variations can be apparent from the foregoing descriptions without departing from the spirit and scope of the invention as defined in the appended claims.

What is claimed is:

1. A medical device comprising:
    a mouthpiece in fluid connectivity with a flow chamber housing;
    a spring-loaded vane mounted for pivoting bidirectional movement about an axis in a central portion of the flow chamber housing, the spring-loaded vane comprising at least one light pipe for transmitting light from a light source to an interior wall of the flow chamber housing; and
    a sensor transmission module housing detachably coupled to the flow chamber housing, the sensor transmission housing comprising:
    the light source operative for emitting light onto the interior wall of the flow chamber housing via the at least one light pipe;
    an image sensor coupled to a digital signal processor, wherein the image sensor is configured for:
    receiving reflected light from the interior wall of the flow chamber housing; and
    capturing images based on the received reflected light;
    the digital signal processor operatively coupled to at least one processor, the digital signal processor configured for receiving the images from the image sensor and determining coordinates corresponding to displacement of the spring-loaded vane; and
    the at least one processor operatively coupled to a transmitter, the at least one processor configured for transmitting, via the transmitter, text data comprising the determined coordinates and an identifier associated with the medical device to a mobile device for further transmission to at least one server for processing.

2. The medical device of claim 1, wherein the light source is a light-emitting diode.

3. The medical device of claim 1, wherein the light source is a laser diode.

4. The medical device of claim 1, wherein the light source and the image sensor are a single device.

5. The medical device of claim 1, wherein the light pipe is aligned with an axis that extends diagonally from a bottom of the spring-loaded vane to a top of the spring-loaded vane.

6. The medical device of claim 1, wherein the at least one processor is configured for receiving the determined coordinates from the digital signal processor, converting the determined coordinates to text data, encrypting the text data, and creating a data package comprising the encrypted text data and the identifier associated with the medical device.

7. The medical device of claim 6, wherein the at least one server is configured for analyzing the text data based at least in part on the identifier associated with the medical device.

\* \* \* \* \*